US007541458B2

(12) United States Patent
Vu et al.

(10) Patent No.: US 7,541,458 B2
(45) Date of Patent: *Jun. 2, 2009

(54) β-LACTAM SYNTHESIS

(75) Inventors: Phong Vu, Little Falls, NJ (US); Robert A. Holton, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/449,462

(22) Filed: Jun. 8, 2006

(65) Prior Publication Data

US 2006/0281914 A1 Dec. 14, 2006

Related U.S. Application Data

(60) Provisional application No. 60/708,929, filed on Aug. 17, 2005, provisional application No. 60/689,425, filed on Jun. 10, 2005.

(51) Int. Cl.
*C07D 205/08* (2006.01)
(52) U.S. Cl. .................................... 540/200
(58) Field of Classification Search ................ 540/200, 540/354

See application file for complete search history.

(56) References Cited

U.S. PATENT DOCUMENTS

| | | | |
|---|---|---|---|
| 5,175,315 A | 12/1992 | Holton | |
| 5,294,737 A | 3/1994 | Ojima | |
| 5,723,634 A * | 3/1998 | Holton | ............ 549/510 |
| 2004/0132991 A1 | 7/2004 | Naidu | |

FOREIGN PATENT DOCUMENTS

EP           0 442 576 A1        8/1991

OTHER PUBLICATIONS

Cahard, D.; Duhamel, P. Eur. J. Org. Chem. 2001, 1023-1031.*
Bordwell et. al. J. Org. Chem. 1980, 45, 3295.*
Sefcik et. al. Journal of Non-Crystalline Solids 1999, 258, 187-197.*
Kuo et. al. J. Am. Chem. Soc. 1971, 4604-05.*
March, J. Advanced Organic Chemistry, 1985, Wiley, 3rd edition, 908-909.*
Zimmerman, H. E. in Molecular Rearrangements, Chapter 6, Wiley, Paul DeMayo Ed. p. 378-387.*
Bertha, Ferenc; Fetter, Jozsef; Kajtar-Peredy, Maria; Lempert, Karoly "Simple and condensed .beta.-lactams. Part 33.AICI3 catalyzed ring closures of some 3-aryloxy-4-oxoazetidine-2-carboxylic chlorides to 1H-chromeno[3,2-b]azete-2,8(2aH,8aH)-diones and some reactions of the products." Tetrahedron 1999, 55, 5567-5580.*
Gluchowski et. al. Journal of Organic Chemistry 1980 45, 3413-3416.*
Georg et. al. Journal of Medicinal Chemistry 1996, 39, 2705-2709.*
Panunzio "Synthesis and Use of N-(Trimethylsilyl)imines" Organic Process Research & Development 1998, 2, 49-59.*
Dubois Tetrahedron Letters 1984, 41, 4655-4658.*
Hart D. J. "Preparation of Primary Amines and 2-Azetidinones via N-Trimethylsilyl Imines" Journal of Organic Chemistry 1983, 48, 289-294.*
Andreoli, P., et al., "A Synthetic Approach to Azetidinones from Nitriles and Lithiumtriethoxyaluminium Hydride," Tetrahedron Letters, 1986, pp. 1695-1698, vol. 27, No. 15.
Andreoli, P., et al., "Reaction of Silylimines with Ester Enolates. Synthesis of N-Unsubstituted Azetidinones Starting from Nitriles," Journal of the Chemical Society. Perkin Transactions I, Apr. 1988, pp. 945-948, vol. 1, No. 4.
Cainelli G., et al., "β-Lactams from Ester Enolates and Silylimines: Enantioselective Synthesis of (+)-PS-5," J. Am. Chem. Soc., 1988, pp. 6879-6880, vol. 110.
Hart, D. J., et al., "Asymmetric Synthesis of β-Lactams and the Carbapenem Antibiotic (+)-PS-5," J. Am Chem. Soc., 1986, pp. 6054-6056, vol. 108, No. 19.
Hart, D. J., et al., "The Ester Enolate-Imine Condensation Route to β-Lactams," Chem. Rev., 1989, pp. 1447-1465, vol. 89, No. 7.
Hattori, K., et al., "Practical Preparation of α-Hydroxy-β-Amino Ester Units; Stereoselective Synthesis of Taxol Side Chain and Norstatine," Tetrahedron, 1994, pp. 2785-2792, vol. 50, No. 9.
Kobayashi, S., et al., "One-pot Synthesis of β-Amino Esters from Aldehydes Using Lanthanide Triflate as a Catalyst," Tetrahedron Letters, 1995, pp. 5773-5776, vol. 36, No. 32.
P. Andreoli et al., β-Lactams from Ester Enolates and Silylimines: Enantioselective Synthesis of the trans-Carbapenem Antibiotics (+)-PS-5 and (+)-PS-6, Journal of Organic Chemistry, 1991, 56, pp. 5984-5990.
International Search Report for PCT/US2006/022267 dated Feb. 7, 2007, 2 pages.
Fujisawa, H., et al., "Lewis Base Catalyzed Mannich-Type Reactions Between Trimethylsilyl Enol Ethers and Aldimines," Chemistry A European Journal, 2006, pp. 5082-5093, vol. 12.
Rendler, S., et al., "Hypervalent Silicon as a Reactive Site in Selective Bond-Forming Processes," Synthesis, 2005, pp. 1727-1747, vol. 11.
Takahashi, E., et al., "One-Pot Synthesis of β-Lactams from Aldimines and Ketene Silyl Acetals by Tandem Lewis Base-Catalyzed Mannich-Type Addition and Cyclization," Chemistry Letters, Jan. 15, 2005, pp. 216-217, vol. 34, No. 2.

* cited by examiner

*Primary Examiner*—Rita J Desai
*Assistant Examiner*—David K O'Dell
(74) *Attorney, Agent, or Firm*—Bryan Cave LLP

(57) ABSTRACT

The present invention is directed to a process for the preparation of β-lactams. Generally, an imine is cyclocondensed with a ketene acetal or enolate to form the β-lactam product in a "one pot" synthesis, this process is generally performed at a higher temperature than conventional processes.

18 Claims, No Drawings

β-LACTAM SYNTHESIS

REFERENCE TO RELATED APPLICATIONS

This application claims the priority of U.S. provisional application Ser. No. 60/689,425, filed Jun. 10, 2005 and Ser. No. 60/708,929, filed Aug. 17, 2005, hereby incorporated herein by reference in their entirety.

BACKGROUND

The present invention is generally directed to an improved synthetic process for the preparation of β-lactams.

β-lactams have utility in a variety of applications. They possess biological activity and are used, as such, for certain applications. They also serve as synthetic intermediates for a variety of other biologically active compounds.

In *Chem. Rev.* 1989, 89, 1447-1465, Hart et al. describe the use of enolate-imine condensation reactions to prepare, β-lactams. These routes include the use of zinc enolates and Reformatsky reagents as well as reaction of metal and boron enolates with unsaturated nitrogen-containing compounds. In particular, Hart et al. disclose the reaction of N(trimethylsilyl) imines with a lithium enolate of ethyl butyrate to produce a N-unsubstituted-3-ethyl-4-propyl-azetidin-2-one. Generally, due to the decomposition of the intermediates, the reactions require temperature conditions of −78° C.

In U.S. Pat. No. 5,723,634, Holton et al. describe a synthetic pathway for the preparation of N-unsubstituted- and N-substituted-3-hydroxy β-lactams. A lithium enolate (prepared from ethyl triethylsiloxyacetate and lithium diisopropyl amide) cyclocondenses with an imine (prepared from an aryl aldehyde and lithium hexamethyldisilazide) to produce a 3-triethylsiloxy-4-arylazetidin-2-one. The resulting arylazetidin-2-one can be converted to a N-benzoyl β-lactam by treatment with benzoyl chloride in the presence of a base.

SUMMARY

Among the various aspects of the present invention is a process for preparing β-lactams having fewer steps and which may be carried out at a higher temperature than conventional processes.

One aspect is a process for the preparation of a β-lactam corresponding to Formula 1. The process comprises treating an imine corresponding to Formula 2 with a ketene (thio) acetal corresponding to Formula 3 in the presence of an alkoxide or siloxide

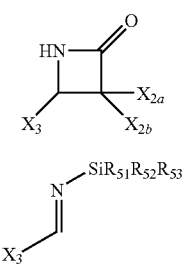

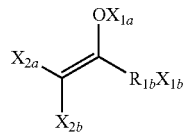

wherein
- $X_{1a}$ a silyl protecting group, metal, or comprises ammonium;
- $X_{1b}$ is a sulfhydryl or hydroxyl protecting group;
- $X_{2a}$ is hydrogen, alkyl, alkenyl, alkynyl, aryl, heterocyclo, —$OX_6$, —$SX_7$, or —$NX_8X_9$;
- $X_{2b}$ is hydrogen, alkyl, alkenyl, alkynyl, aryl, heterocyclo, —$OX_6$, or —$SX_7$;
- $X_3$ is alkyl, alkenyl, alkynyl, aryl or heterocyclo;
- $X_6$ is alkyl, alkenyl, alkynyl, aryl, heterocyclo, or hydroxyl protecting group;
- $X_7$ is alkyl, alkenyl, alkynyl, aryl, heterocyclo, or sulfhydryl protecting group;
- $X_8$ is hydrogen, hydrocarbyl, substituted hydrocarbyl, or heterocyclo;
- $X_9$ is hydrogen, amino protecting group, hydrocarbyl, substituted hydrocarbyl, or heterocyclo;
- $R_{1b}$ is oxygen or sulfur; and
- $R_{51}$, $R_{52}$ and $R_{53}$ are independently alkyl, aryl, or aralkyl;
- provided, however, that $X_{1b}$ is a silyl protecting group when $X_{1a}$ is metal and $R_{1b}$ is oxygen.

Other objects and features will be in part apparent and in part pointed out hereinafter.

DETAILED DESCRIPTION

In accordance with the process of the present invention, N-unsubstituted-3,4-substituted β-lactams may be prepared in a "one pot" synthesis that occurs at temperatures greater than −78° C. Typically, lithium enolate intermediates used in conventional syntheses of N-unsubstituted-3,4-substituted β-lactams decompose before reaction with the imine at temperatures above −78° C. But, the ketene (thio)acetal intermediates used in the process of the present invention do not decompose at temperatures conveniently achieved using and ice water bath or other ice and solvent mixtures that provide reaction temperatures near 0° C. Advantageously, this approach eliminates the need to isolate intermediates, increases overall yield and efficiency while decreasing reactants used, reaction time and complexity.

In general, an imine is cyclocondensed with a ketene (thio) acetal in the presence of an alkoxide or siloxide to form the β-lactam product. A preferred embodiment of this cyclocondensation reaction is illustrated in Reaction Scheme 1 tin which imine 2 is cyclocondensed with ketene (thio)acetal 3 in the presence of an alkoxide or siloxide to produce β-lactam 1.

Reaction Scheme 1

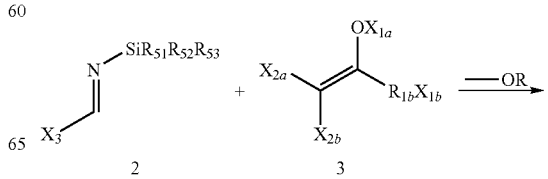

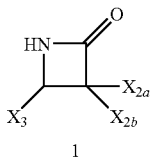

wherein $X_{1a}$, $X_{1b}$, $X_{2a}$, $X_{2b}$, $X_3$, $R_{1b}$, $R_{51}$, $R_{52}$ and $R_{53}$ are as previously defined, and —OR is an alkoxide or siloxide ion. The ketene (thio)acetal is commercially available or may be prepared in situ from a carboxylic acid and the imine may be prepared in situ from commercially available aldehydes and disilazides.

β-lactams

One aspect of the present invention is the preparation of β-lactams corresponding to Formula 1. In turn, β-lactams corresponding to Formula 1 may be N-acylated or N-silylated to produce β-lactams corresponding to Formula 1A:

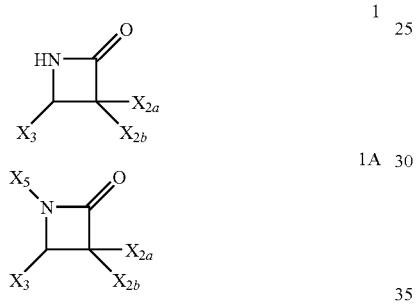

wherein
 $X_{2a}$, $X_{2b}$, $X_3$, and $X_8$ are as previously defined in connection with Formula 1;
 $X_5$ is —COX$_{10}$, —COOX$_{10}$ or —CONX$_8$X$_{10}$, or —SiR$_{51}$R$_{52}$R$_{53}$;
 $X_{10}$ is hydrocarbyl, substituted hydrocarbyl or heterocyclo; and
 $R_{51}$, $R_{52}$, and $R_{53}$ are independently alkyl, aryl or aralkyl.

In one embodiment, $X_{2a}$ is —OX$_6$ and $X_6$ is hydroxyl protecting group. For example, $X_{2a}$ may be —OX$_6$, $X_6$ is —SiR$_{21}$R$_{22}$R$_{23}$, and $R_{21}$, $R_{22}$ and $R_{23}$ are independently alkyl, aryl or aralkyl. In one preferred embodiment, $X_{2a}$ is —OX$_6$, $X_6$ is —SiR$_{21}$R$_{22}$R$_{23}$, and $R_{21}$, $R_{22}$ and $R_{23}$ are independently methyl, ethyl, propyl, phenyl or benzyl.

Similarly, although $X_{2b}$ may be hydrogen, alkyl, alkenyl, alkynyl, aryl, heterocyclo, —OX$_6$, or —SX$_7$, in one embodiment, $X_{2b}$ is preferably hydrogen or alkyl. More preferably, $X_{2b}$ is hydrogen.

In one embodiment, $X_3$ is alkyl, alkenyl, aryl, or heterocyclo. In a further embodiment, $X_3$ is alkyl, alkenyl, phenyl, or heterocyclo. For example, $X_3$ may be cycloalkyl such as isopropyl, alkenyl such as isobutenyl, or heterocyclo such as furyl or thienyl. In one preferred embodiment, $X_3$ is phenyl, furyl, or thienyl.

In one preferred embodiment, $X_5$ is —COX$_{10}$ and $X_{10}$ is alkyl, alkenyl or aryl; for example, $X_5$ may be —COX$_{10}$ and $X_{10}$ is phenyl. In an alternative embodiment, $X_5$ is —COOX$_{10}$ and $X_{10}$ is alkyl; for example, $X_5$ may be —COOX$_{10}$ and $X_{10}$ is n-propyl, isopropyl, n-butyl, isobutyl, or tert-butyl. In one preferred embodiment, $X_5$ is —COOX$_{10}$ and $X_{10}$ is tert-butyl.

Alternatively, $X_5$ is —SiR$_{51}$R$_{52}$R$_{53}$, $R_{51}$, $R_{52}$, and $R_{53}$ are preferably independently alkyl; more preferably, $R_{51}$, $R_{52}$, and $R_{53}$ are independently methyl, ethyl, propyl, or butyl; still more preferably, $R_{51}$, $R_{52}$, and $R_{53}$ are methyl.

In combination, among the preferred embodiments are β-lactams corresponding to Formula 1 and 1A wherein $X_{2a}$ is —OX$_6$ wherein $X_6$ is hydroxyl protecting group, $X_{2b}$ is hydrogen, $X_3$ is alkyl, aryl or heterocyclo, and preferably, cycloalkyl, more preferably, phenyl, furyl or thienyl; and $X_5$ is hydrogen, alkylcarbonyl, alkenylcarbonyl, aroyl or alkoxycarbonyl, preferably, benzoyl, alkoxycarbonyl, more preferably, benzoyl, n-propoxycarbonyl, isopropoxycarbonyl, isobutoxycarbonyl or tert-butoxycarbonyl. In certain embodiments, $X_{2b}$ is hydrogen, $X_3$ is phenyl, and $X_{2a}$ is —OX$_6$ wherein $X_6$ is —SiR$_{21}$R$_{22}$R$_{23}$ wherein $R_{21}$, $R_{22}$ and $R_{23}$ are independently alkyl, preferably, $R_{21}$, $R_{22}$ and $R_{23}$ are independently methyl, ethyl, or propyl.

Imines

As depicted in Reaction Scheme 1, β-lactams corresponding to Formula 1 may be prepared from an imine corresponding to Formula 2

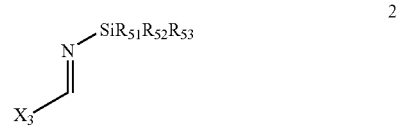

wherein
 $R_{51}$, $R_{52}$ and $R_{53}$ are independently alkyl, aryl or aralkyl; and
 $X_3$ is as defined above in connection with Formula 1.

In certain embodiments, $R_{51}$, $R_{52}$ and $R_{53}$ are independently alkyl or aryl. For example, $R_{51}$, $R_{52}$ and $R_{53}$ may independently be methyl, ethyl, propyl, butyl, phenyl or benzyl; preferably, $R_{51}$, $R_{52}$ and $R_{53}$ are independently methyl, ethyl or propyl. Preferred substituent groups for $X_3$ are detailed above in connection with Formulae 1 and 1A.

In combination, preferred substituent groups are $R_{51}$, $R_{52}$ and $R_{53}$ are independently alkyl or aryl. Preferably, $R_{51}$, $R_{52}$ and $R_{53}$ are independently methyl, ethyl, propyl, butyl, phenyl or benzyl, more preferably, $R_{51}$, $R_{52}$ and $R_{53}$ are methyl, ethyl or propyl. In these embodiments, $X_3$ is alkyl, aryl or heterocyclo, preferably, cycloalkyl, more preferably, phenyl, furyl, or thienyl.

Generally, imines of Formula 2 described above can be prepared from an aldehyde and a disilazide reagent. The aldehyde has the general Formula of $X_3C(O)H$ wherein $X_3$ is defined above for Formula 1 and the disilazide has the general Formula of $MN(Si(R_{51}R_{52}R_{53}))_2$ wherein M is a positive ion. For example, M is a metal or comprises ammonium. In particular, the metal may be a Group IA, IIA, transition (including lanthanides and actinides), IIB, IIIA IVA, VA, or VIA metal (GAS version). The ammonium comprising substituent is preferably tetraalkylammonium and the alkyl component of the tetraalkylammonium substituent is preferably $C_1$-$C_{10}$ alkyl such as methyl, ethyl, propyl, or butyl. $R_{51}$, $R_{52}$ and $R_{53}$ are defined as above in connection with Formula 2. Typically, the electron-rich nitrogen atom of the disilazide reagent attacks the carbonyl carbon of the aldehyde to form an imine. This preparation reaction proceeds with a wide range of aldehyde substituents as well as a variety of silyl groups attached to the nitrogen. In one embodiment, the disilazide reagent is lithium hexamethyl disilazide (LHMDS) or sodium hexamethyl disilazide (NaHMDS).

Ketene (Thio)Acetals and Enolates

As depicted in Reaction Scheme 1, imines corresponding to Formula 2 are reacted with ketene (thio)acetals corresponding to Formula 3 to produce β-lactams corresponding to Formula 1, the ketene (thio)acetals or enolates corresponding to Formula 3 have the structure

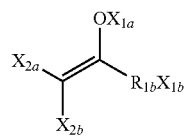

3 wherein $R_{1b}$, $X_{1a}$, $X_{1b}$, $X_{2a}$ and $X_{2b}$ are as previously defined.

When $R_{1b}$ is oxygen, Formula 3 corresponds to a ketene acetal or an enolate. When $R_{1b}$ is sulfur, Formula 3 corresponds to a ketene thioacetal or enolate. In general, it is preferred that $R_{1b}$ be oxygen and that the ketene acetal corresponds to formula $3^{Ox}$:

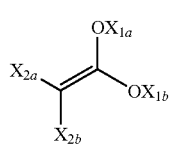

$3^{Ox}$ wherein $X_{1b}$ is a hydroxyl protecting group. In other embodiments, an enolate ($X_{1b}$ is a metal or comprises ammonium) can be used.

In one embodiment, $X_{1a}$ is silyl hydroxyl protecting group having the formula —$SiR_{11}R_{12}R_{13}$ wherein $R_{11}$, $R_{12}$, and $R_{13}$ are independently alkyl or aryl. In this embodiment, $R_{11}$, $R_{12}$, and $R_{13}$ are preferably methyl, ethyl, propyl, butyl, phenyl or benzyl. More preferably, in this embodiment $R_{11}$, $R_{12}$, and $R_{13}$ are methyl, ethyl or propyl. In one particular embodiment, $X_{1a}$ is trimethylsilyl.

Although $X_{2a}$ may be hydrogen, alkyl, alkenyl, alkynyl, aryl, heterocyclo, —$OX_6$, —$SX_7$ or —$NX_8X_9$, and $X_{2b}$ may be hydrogen, alkyl, alkenyl, alkynyl, aryl, heterocyclo, —$OX_6$, or —$SX_7$, it is generally preferred that one (and only one) of $X_{2a}$ and $X_{2b}$ be hydrogen. In addition, it is generally preferred that one of $X_{2a}$ and $X_{2b}$ be —$OX_6$ and that $X_6$ be a hydroxyl protecting group. In one preferred embodiment, therefore, ketene (thio)acetal or enolate 3 is a ketene acetal corresponding to Formula 3A

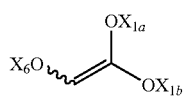

3A wherein $X_{1a}$ is a silyl hydroxyl protecting group and $X_{1b}$ and $X_6$ are hydroxyl protecting groups. In one preferred embodiment, $X_{1a}$ is —$SiR_{11}R_{12}R_{13}$, $X_{1b}$ is —$SiR_{14}R_{15}R_{16}$ and $X_6$ is —$SiR_{21}R_{22}R_{23}$ wherein $R_{11}$, $R_{12}$, $R_{13}$, $R_{14}$, $R_{15}$, $R_{16}$, $R_{21}$, $R_{22}$ and $R_{23}$ are independently alkyl. For example, $R_{11}$, $R_{12}$, $R_{13}$, $R_{14}$, $R_{15}$, $R_{16}$, $R_{21}$, $R_{22}$ and $R_{23}$ may independently be methyl, ethyl or propyl. In one preferred embodiment, ketene (thio) acetal 3 corresponds to Formula 3A, $X_{1a}$ is trimethylsilyl, $X_{1b}$ is —$SiR_{14}R_{15}R_{16}$, $X_6$ is —$SiR_{21}R_{22}R_{23}$ and $R_{14}$, $R_{15}$, $R_{16}$, $R_{21}$, $R_{22}$ and $R_{23}$ are independently alkyl.

In one embodiment, $X_{2a}$ is —$OX_6$ wherein $X_6$ and $X_{1a}$, in combination, form a bridging silyl protecting group having the formula —$Si(R_{21}R_{22})OSi(R_{11}R_{12})$— wherein $R_{11}$, $R_{12}$, $R_{21}$ and $R_{22}$ are independently alkyl or aryl. This is illustrated by Formula 33:

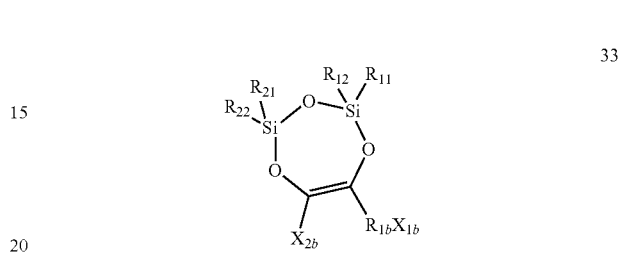

33 wherein $R_{1b}$, $X_{1b}$, $X_{2b}$ are as previously defined.

As noted, $R_{1b}$ may be oxygen or sulfur and $X_{1b}$ may be sulfhydryl or hydroxyl protecting group. In one preferred embodiment, however, $R_{1b}$ is oxygen where $X_{1b}$ is hydroxyl protecting group, more preferably, silyl hydroxyl protecting group, even more preferably, trimethylsilyl or triethylsilyl. In another embodiment, $R_{11}$, $R_{12}$, $R_{21}$, and $R_{22}$ are independently alkyl, preferably, independently methyl, ethyl, or propyl.

Generally, the ketene acetals of Formulae 3 and 3A can be prepared from a carboxylic acid as depicted in Scheme 2. As illustrated, Reaction Schemes 2 and 3 depict the preparation of ketene acetals, but substitution of a sulfur for oxygen to produce a ketene thioacetal is possible. First, for example, the carboxylic acid is protected with a hydroxyl protecting group to form a protected ester. Next, the protected ester is treated with a disilazide agent (e.g., lithium or sodium) and a silyl protecting group to form a ketene acetal.

Scheme 2

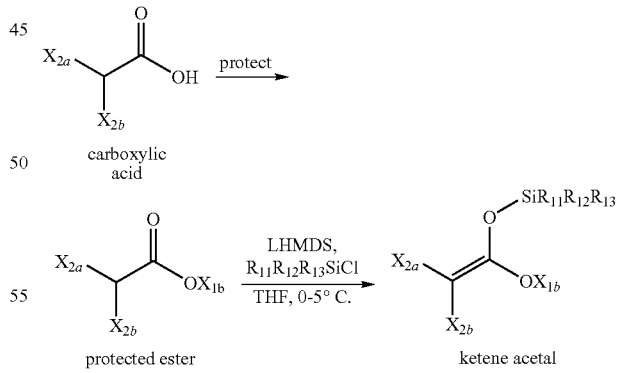

In one embodiment, preferably, $X_{2a}$ is —$OX_6$ wherein $X_6$ is —$Si(CH_3)_3$ and $X_{2b}$ is hydrogen. In this case, the carboxylic acid is treated with trimethylsilyl chloride to produce a trimethylsilyl ester (e.g., $X_{1b}$ is —$Si(CH_3)_3$). The trimethylsilyl ester can then be contacted with LHMDS or NaHMDS and preferably, trimethylsilyl chloride (or other hydroxyl protecting group) to produce a ketene acetal of Formula 3 wherein $R_{11}$, $R_{12}$ and $R_{13}$ are methyl. In one exemplary embodiment, the ketene acetal of Formula 3 is tris(trimethylsilyloxy)ethene which can be prepared from glycolic acid and trimethylsilyl chloride or is available commercially from Aldrich.

In other embodiments, an enolate, rather than a ketene (thio)acetal can be used. For example, the enolate having a structure corresponding Formula 4

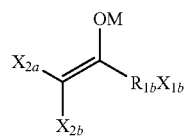
4 wherein M is a metal or comprises ammonium; $R_{1b}$, $X_{1b}$, $X_{2a}$, and $X_{2b}$ are as defined above in connection with Formula 3. Exemplary metal and ammonium-containing ions are described above in connection with the disilazide agent. In one preferred embodiment, the metal is a lithium ion.

Reaction of an Imine and a Ketene (Thio)Acetal to Produce a β-lactam

For the process of the present invention, the structures of the products (e.g., β-lactams) and reactants (e.g., imines and ketene (thio)acetals or enolates) are described above. This process produces the desired β-lactam product by treating an imine with a ketene (thio)acetal or enolate in the presence of an alkoxide or siloxide. The alkoxide or siloxide can be generated in situ or can be introduced to the reaction mixture. Without being bound by theory, it is hypothesized that the alkoxide or siloxide interacts with the ketene (thio)acetal to form a reactive intermediate that facilitates β-lactam formation. Generally, the alkoxide or siloxide is associated with a positive ion and the alkoxide has the formula $^{-OR}{}_a$ wherein $R_a$ is hydrocarbyl, substituted hydrocarbyl, or heterocyclo, and the siloxide has the formula $^{-OSiR}{}_{51}R_{52}R_{53}$ wherein $R_{51}$, $R_{52}$, and $R_{53}$ are defined as above in connection with Formula 2. Exemplary positive ions (M⁺) are metal and ammonium-containing ions as described above in connection with the disilazide agent. In various preferred embodiments, the alkoxide or siloxide is generated in situ. One way to generate the alkoxide or siloxide in situ is by treating an aldehyde ($X_3C(O)H$) with a disilazide ($MN(SiR_{51}R_{52}R_{53})_2$). These species are described in more detail above in the discussion of the imine reactant. In many of these embodiments, the alkoxide or siloxide is $^-OSi R_{51}R_{52}R_{53}$, particularly, $^-OTMS$.

Further, this process can occur in one vessel without isolation of intermediates. However, depending on the starting materials and the β-lactam product, the order of addition of reactants may vary. For example, when a carboxylic acid is used as a starting material for the ketene acetal, the production of the ketene acetal occurs according to Scheme 2 above. At 0° C. to 5° C., Z- and E-lithium enolate intermediates decompose faster than they react with an imine to form a β-lactam. Alternatively to reaction of the lithium enolates with an imine, the lithium enolates can be further reacted with a silyl chloride to produce a ketene acetal. In this case, the ketene acetal is produced in situ or is commercially available and undergoes cyclocondensation with the imine product of an aldehyde (e.g., $X_3C(O)H$) and a disilazide (e.g., $MN(SiR_{51}R_{52}R_{53})_2$ such as LHMDS or NaHMDS) to produce cis- and trans-β-lactams in high yield (see Scheme 3).

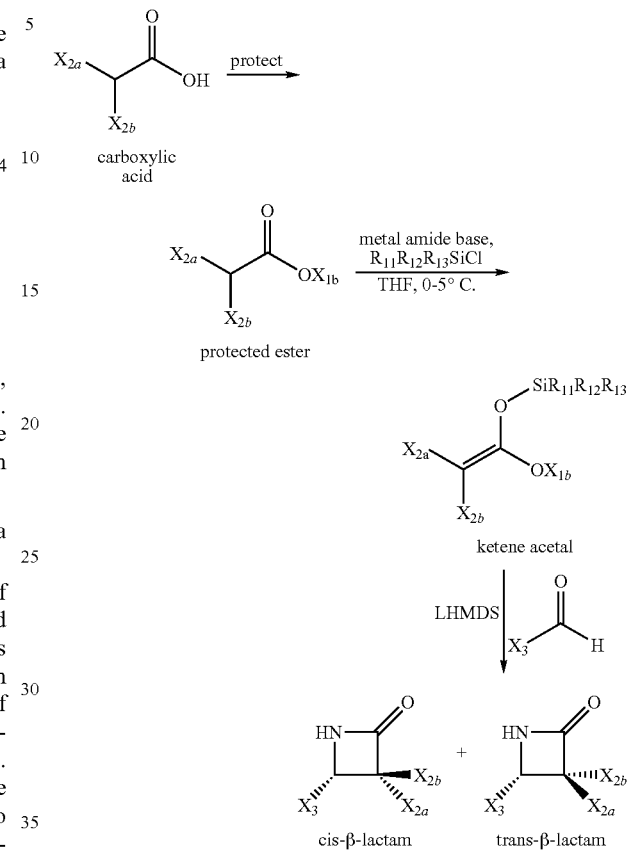

In one exemplary embodiment of scheme 3, $R_{11}$, $R_{12}$ and $R_{13}$ are methyl, $X_{1b}$ is hydroxyl protecting group, $X_{2a}$ is —$OX_6$, $X_{2b}$ is hydrogen, $X_3$ is phenyl, furyl or thienyl and $X_6$ is hydroxyl protecting group. In a more preferred embodiment of scheme 3, $R_{11}$, $R_{12}$ and $R_{13}$ are methyl, $X_{1b}$ is —Si(CH$_3$)$_3$, $X_{2a}$ is —$OX_6$, $X_{2b}$ is hydrogen, $X_3$ is phenyl, furyl or thienyl and $X_6$ is —Si(CH$_3$)$_3$.

Alternatively to the reaction pathway presented in scheme 3, when the desired ketene acetal is available commercially, the following reaction scheme 4 is used to prepare the desired β-lactam. Typically, an aldehyde (e.g., $X_3C(O)H$) is treated with a strong base (e.g., $MN(SiR_{51}R_{52}R_{53})_2$ such as LHMDS or NaHMDS) to produce an imine that is contacted in situ with a ketene acetal to produce the desired β-lactams. In one embodiment of scheme 4, preferably, $R_{51}$, $R_{52}$ and $R_{53}$ are methyl.

Scheme 4

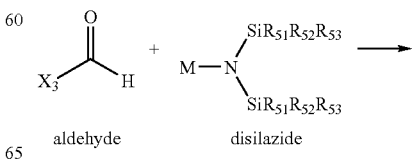

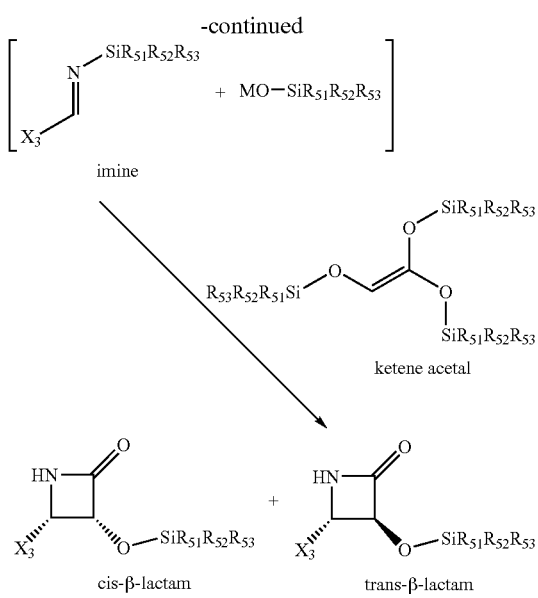

Yet another alternative is reaction of an enolate with an imine to form a β-lactam as depicted in Scheme 5. In this reaction pathway, the protected ester is reacted with a disilazide in a polar aprotic solvent at 0-5° C. to form the Z- and E-enolates. The enolate solution is then cooled to −25° C. to −30° C. and an excess of enolate is contacted with a solution of the reaction product of an aldehyde and a disilazide. The temperature of the reaction mixture is kept below about −25° C. for about 1 to 2 hours before warming the reaction mixture to about −5° C. to 0° C.

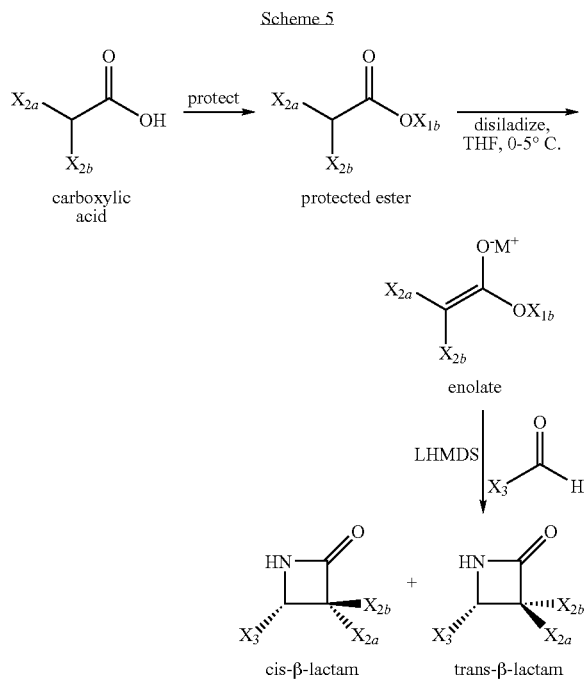

Preferably, the solvent for the transformation is a polar aprotic solvent. Our experience to date suggests non-polar chlorinated solvents such as dichloromethane and chloroform tend to lead to low conversion rates. Exemplary polar aprotic solvents are tetrahydrofuran (THF), diethyl ether, 1,2-dimethoxyethane (DME), dimethylformamide (DMF), and the like. In some of the various embodiments, the polar aprotic solvent is DME.

In general, whether the reaction pathway follows schemes 3, 4, or 5, once the reaction between the imine and the ketene acetal or between the imine and the enolate is complete, the reaction can be quenched. The quenching, for example, can be accomplished by addition of a quenching reagent. Depending on the selection of the quenching reagent, the C3 silyl-protected hydroxyl group will either remain protected or will be deprotected during the quenching procedure. For example, when the reaction is quenched by neutralization with glacial acetic acid, it is necessary to deprotect the C3 hydroxyl group in an additional step, for example, by methanolysis in the presence of a catalytic amount of sodium carbonate. In contrast, when the reaction is quenched by addition of saturated sodium bicarbonate, the C3 hydroxyl group is deprotected in the course of the quenching reaction.

Once the reaction is quenched, the desired β-lactam product is isolated by addition of an organic solvent followed by separation of the organic layer containing the desired product from the aqueous layer. Subsequently, the organic layer(s) can be washed with water and brine.

Finally, the organic layer can be dried, filtered and concentrated. The organic layer can be dried using chemical dessicants such as sodium sulfate, molecular sieves or another similar substance. Typically, the organic layer is filtered through a pad of silica, however, celite or another similar substance could be used. Generally, the organic layer is concentrated by rotary evaporation, but a similar method of removing solvent, such as stirring under high vacuum or the like could be used.

Once the desired N-unsubstituted β-lactams of Formula 1 are produced, they can be converted to N-substituted β-lactams of Formula 1A by contact with an appropriate reagent. For example, the —NH moiety of the β-lactam of Formula 1 can be reacted with an amino protecting group to form an amido moiety, a carbamate moiety, a thiocarbamate moiety, a urea moiety, and the like. Further, the moieties produced from the protection reaction can be incorporated into the final product. Exemplary reagents for this transformation are dicarbonates (e.g., di-tert-butyl dicarbonate), haloformates (e.g., methyl chloroformate, ethyl chloroformate, propyl chloroformate, isopropyl chloroformate, butyl chloroformate, isobutyl chloroformate, pentyl chloroformate), acid halides (acetyl chloride, ethanoyl chloride, propanoyl chloride, butanoyl chloride, propanoyl chloride) and the like.

Further, when a protected hydroxyl group is present in the C3 position (e.g., $R_2$), the hydroxyl group can be deprotected to form an unprotected hydroxyl group and further derivatization of the active C3 hydroxyl group can occur. In one embodiment, methanolysis of the hydroxyl group is achieved in the presence of a catalytic amount of sodium carbonate. Generally, methods are known for removing a silyl protecting group. Once the protecting group is removed, for example, the unprotected hydroxyl group can be esterified, alkylated, arylated to produce a variety of β-lactam derivatives.

Uses of β-lactams

Generally, β-lactams are biologically active and can be used as synthetic intermediates to produce biologically active compounds. For example, antibiotics such as penicillins, cephalosporins, penems, trinems and their derivatives contain a β-lactam ring structure. In addition, β-lactams have been discovered to have biological properties other than antibiotic efficacy. β-lactams can serve as inhibitors of serine proteases, such as human leukocyte elastase (HLE) or thrombin, acyl-CoA cholesterol acyltransferase inhibitors and inhibitors of human cytomegalovirus.

In addition, β-lactams are used as synthetic intermediates and have been used to prepare aromatic β-amino acids and their derivatives, peptides, polyamines, polyamino alcohols, amino sugars and polyamino ethers. Generally, the ring strain of the four-membered β-lactam ring is exploited to prepare a variety of chirally enhanced compounds resulting from ring opening. In another example, β-lactams are used to prepare taxol and other taxane derivatives by contact of baccatin III or 10-deacetlyl baccatin III or one of their derivatives with a cis-β-lactam. Generally, in the process of the transformation, an alkoxide moiety at the C-13 position attacks the cis-β-lactam at the ring carbonyl carbon, which causes the β-lactam ring to open to produce the C-13 side chain (e.g., an isoserine ester).

Definitions

The term "acyl," as used herein alone or as part of another group, denotes the moiety formed by removal of the hydroxyl group from the group —COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

Unless otherwise indicated, the alkyl groups described herein are preferably lower alkyl containing from one to eight carbon atoms in the principal chain and up to 20 carbon atoms. They may be substituted or unsubstituted and straight or branched chain or cyclic and include methyl, ethyl, propyl, butyl, pentyl, hexyl and the like.

Unless otherwise indicated, the chiral alkyl groups described herein are derived from chiral alcohols or chiral oxazolidones. Exemplary chiral alkyl groups are derived from one optical isomer of menthol, neomenthol, borneol, isopinocampheneol, trans-2-phenyl-1-cyclohexanol, 10-dicyclohexylsulfamoyl-D-isoborneol, 8-phenylmenthol, cinchonine, cinchonidine, quinine, quinidine, N-methylephedrine and 4-isopropyloxazolylidin-2-one.

Unless otherwise indicated, the alkenyl groups described herein are preferably lower alkenyl containing from two to eight carbon atoms in the principal chain and up to 20 carbon atoms. They may be substituted or unsubstituted and straight or branched chain or cyclic and include ethenyl, propenyl, butenyl, pentenyl, hexenyl, and the like.

Unless otherwise indicated, the alkynyl groups described herein are preferably lower alkynyl containing from two to eight carbon atoms in the principal chain and up to 20 carbon atoms. They may be substituted or unsubstituted and straight or branched chain and include ethynyl, propynyl, butynyl, pentynyl, hexynyl, and the like.

The "amino protecting groups" described herein are moieties that block reaction at the protected amino group while being easily removed under conditions that are sufficiently mild so as not to disturb other substituents of the various compounds. For example, the amino protecting groups may be carbobenzyloxy (Cbz), t-butoxycarbonyl (t-Boc), allyloxycarbonyl and the like. A variety of protecting groups for the amino group and the synthesis thereof may be found in "Protective Groups in Organic Synthesis" by T. W. Greene and P. G. M. Wuts, John Wiley & Sons, 1999.

The term "aromatic" as used herein alone or as part of another group denote optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "aralkyl" as used herein denote optionally substituted alkyl groups substituted with an aryl group. Exemplary aralkyl groups are substituted or unsubstituted benzyl, ethylphenyl, propylphenyl and the like.

The term "carboxylic acid" refers to a RC(O)OH compound where R can be hydrogen, or substituted or unsubstituted alkyl, alkenyl, alkynyl, aryl, substituted aryl.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms and/or 1 or 2 sulfur atoms in the ring, and is bonded to the remainder of the molecule through a carbon. Exemplary heteroaryls include furyl, thienyl, pyridyl, oxazolyl, isoxazolyl, oxadiazolyl, pyrrolyl, pyrazolyl, triazolyl, tetrazolyl, imidazolyl, pyrazinyl, pyrimidyl, pyridazinyl, thiazolyl, thiadiazolyl, biphenyl, naphthyl, indolyl, isoindolyl, indazolyl, quinolinyl, isoquinolinyl, benzimidazolyl, benzotriazolyl, imidazopyridinyl, benzothiazolyl, benzothiadiazolyl, benzoxazolyl, benzoxadiazolyl, benzothienyl, benzofuryl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, acyl, acyloxy, nitro, amino, amido, nitro, cyano, ketals, acetals, esters and ethers.

The "hydroxyl protecting groups" described herein are moieties that block reaction at the protected hydroxyl group while being easily removed under conditions that are sufficiently mild so as not to disturb other substituents of the various compounds. For example, the hydroxyl protecting groups may be ethers (e.g., allyl, triphenylmethyl (trityl or Tr), benzyl, p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups for the hydroxyl group and the synthesis thereof may be found in "Protective Groups in Organic Synthesis" by T. W. Greene and P. G. M. Wuts, John Wiley & Sons, 1999.

The "sulfhydryl protecting groups" described herein are moieties that block reaction at the protected sulfhydryl group while being easily removed under conditions that are sufficiently mild so as not to disturb other substituents of the various compounds. For example, the sulfhydryl protecting groups may be silyl esters, disulfides and the like. A variety of protecting groups for the sulfhydryl group and the synthesis thereof may be found in "Protective Groups in Organic Synthesis" by T. W. Greene and P. G. M. Wuts, John Wiley & Sons, 1999.

The following examples illustrate the invention.

EXAMPLES

Example 1

Preparation of Trimethylsilyl 2-(trimethylsilyloxy)acetate

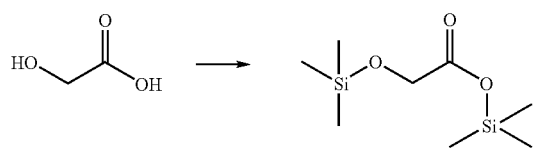

Trimethylsilyl 2-(trimethylsilyloxy)acetate is available from many vendors. However, it can be easily prepared from inexpensive glycolic acid ($75/Kg from Aldrich) and trimethylsilyl chloride ($80/Kg from Aldrich) in the presence of 2 equivalents of pyridine. Typically, glycolic acid (76.05 g, 1 mol) was dissolved in dry pyridine (164 mL, 2 mol) then the mixture was cooled to 0 to 5° C. in an ice-water bath with stirring. Neat trimethylsilyl chloride (108.64 g, 1 mol) was added drop-wise to control the exotherm to less than 40° C. Pyridinium chloride precipitated as a free flowing solid. Heptane (500 mL) was added to aid the agitation. The second equivalent of neat trimethylsilyl chloride was added and the mixture was stirred at ambient 22 to 40° C. for 30 minutes until the reaction was complete. The mixture was further diluted with heptane (1 L) and the salt was allowed to precipitate out. The heptane layer was siphoned into the rotary evaporator through a medium porous inline filter and concentrated to give a clear oil (215 g, 0.98 mol) of the trimethylsilyl 2-(trimethylsilyloxy)acetate. It was distilled in the rotary evaporator at 70 to 75° C. under vacuum of 6 to 8 mmHg.

Example 1A

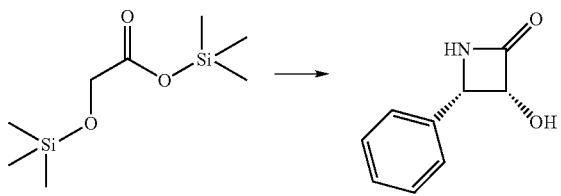

When the reaction of the lithium enolate (made by treating trimethylsilyl-(trimethylsilyloxy)acetate with lithium hexamethyldisilazide) with trimethylsilylbenzaldimine (generated in situ from aldehyde (1a-f below) and lithium hexamethyldisilazide) reported by Hart et al. was examined, the enolate decomposition occurred faster than its reaction with the imine at 0 to 5° C. A solution to this problem was found by lowering the temperature of the enolate's reaction to −25° C. and using an excess (e.g., 2 eqs) amount of the enolate.

Thus, benzaldehyde (5.3 g, 0.05 mol) was added to the 1.0 M solution of LHMDS in THF (150 mL 0.15 mol) at 0° C. and the mixture was stirred for 30 minutes before cooling to −30 to −25° C. Once the reaction temperature was at −30° C., a 1 M solution of the trimethylsilyl 2-(trimethylsiloxy)acetate ester (22.0 g, 0.1 mol, 2 eq) in THF was added drop-wise to control the exotherm to maintain the reaction temperature to <−25° C. The mixture was stirred at this temperature for 1 h before warming to −5 to 0° C. The mixture was stirred at this temperature for 18 h. The mixture was quenched into a saturated solution of sodium bicarbonate (100 mL) and extracted with 1-butanol (500 mL). The 1-butanol was evaporated under vacuum and the residue was taken up in methanol (75 mL) and sodium carbonate (0.5 g, 0.005 mol) for approximately 1 h at ambient temperature. The reaction mixture then was quenched with acetic acid (0.6 g, 0.010 mol), triethylamine (2 g, 0.02 mol), and diluted with 100 mL of ethyl acetate. The mixture was filtered through a pad of silica gel (50 g) and the filtrate was concentrated on a rotary evaporator at 40° C. until crystal formation occurred. The mixture was cooled in a 0° C. ice bath for 30 min and the crystals were collected via vacuum filtration, washed with cold ethyl acetate, and dried to a constant weight of 4.13 g (50% yield); a white powder resulted. mp: 140 to 145° C., $^1$H NMR (400 MHz, CDCl$_3$) δ (ppm): 2.26 (d J=9.4 Hz, 1H), 4.96 (d, 4.96 Hz, 1H), 5.12 (m, 1H), 4.15 (bm, 1H), 7.41 (m, 5H).

Example 2

Preparation of 3-hydroxy-4-substituted-azetidin-2-ones

A 1 M solution of LHMDS in THF (100 mL, 0.1 mol) was cooled to 0° C. and a 1 M solution of trimethylsilyl 2-(trimethylsilyloxy)acetate (22.0 g, 0.1 mol) in THF that was prepared as in Example 1 was added drop-wise to control the exotherm and maintain the temperature at 0° C. to 5° C. To this solution was added 1 equivalent of trimethylsilyl chloride followed by the addition of 1 equivalent of LHMDS and 1 equivalent of benzaldehyde with stirring at 0 to 15° C. over 14 h. The 3-trimethylsilyloxy β-lactam products were observed (via $^1$H NMR of reaction mixture) as a 5:1 cis:trans ratio in quantitative yield. This process is depicted in Scheme 6 below.

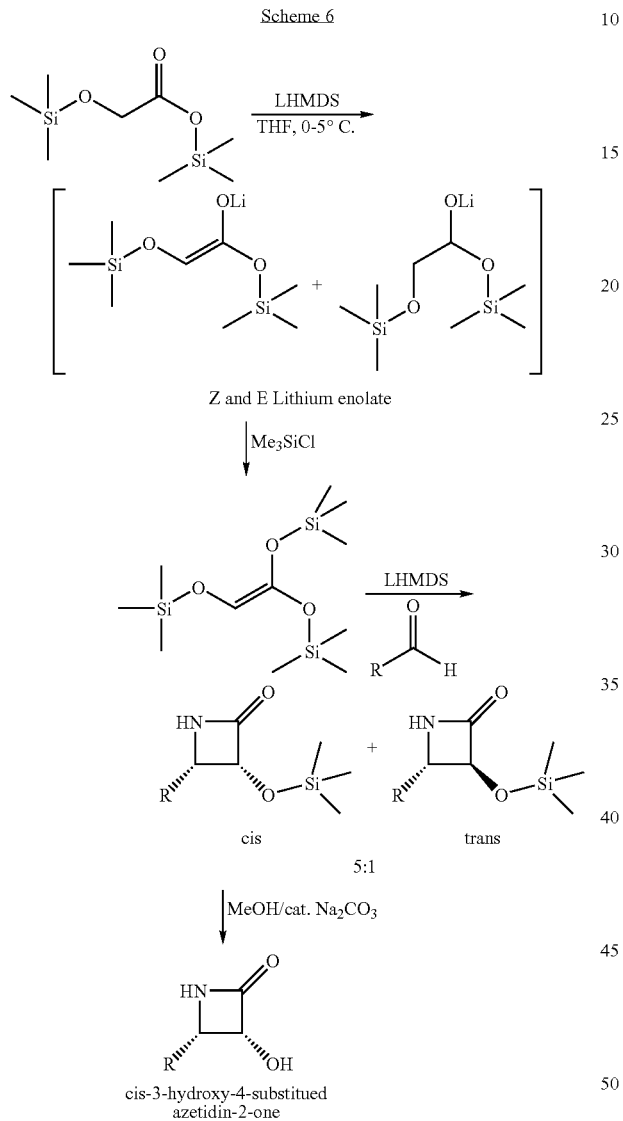

Methanolysis of the silyl ether was easily accomplished in 15 minutes at ambient temperature with a catalytic amount of sodium carbonate and the desired product cis-hydroxy-4-substituted-β-lactam crystallized out in 48% isolated yield upon concentration from ethyl acetate.

Example 3

Preparation of 3-hydroxy-4-thienyl-azetidin-2-one

Typically, a 1.0 M THF solution of lithium hexamethyldisilazide (140 mL, 0.14 mol) under nitrogen was diluted with THF (140 mL) and cooled to 0 to 5° C. with an ice-water bath. The trimethylsilyl 2-(trimethylsilyloxy)acetate (33.4 g, 0.14 mol) was added drop-wise over 20 minutes. To this enolate solution was added trimethylsilylchloride (17.7 mL, 0.14 mol) and after 5 minutes of stirring, a second portion of LHMDS solution in THF (100 mL, 0.10 mol) was added over 10 minutes. To this solution was added 2-thiophenecarboxaldehyde (11.2 g, 0.1 mol) drop-wise over 15 to 20 min to control the exotherm at <5° C. This solution was stirred at 0 to 5° C. over 14 h corresponding to complete disappearance of the imine.

The reaction was neutralized with glacial acetic acid (6 g, 0.10 mol) and diluted with ethyl acetate (400 mL) and transferred to a 2-L separatory funnel. The mixture was washed with water (100 mL) and brine (100 mL). The organic layer was dried over sodium sulfate, filtered through a pad of silica gel and concentrated to give a yellow solid. The solid was taken up in methanol (300 mL) and solid $Na_2CO_3$ (1.0 g) and the mixture was stirred at ambient temperature for 15 min. TLC monitoring eluting with 2:1 ethyl acetate:hexanes showed complete conversion from the non-polar TMS-ether ($R_f$=0.7) to the polar product ($R_f$=0.25). The reaction was quenched with glacial acetic acid (0.6 mL) and the mixture was concentrated to a solid. The solid was dissolved in hot ethyl acetate (500 mL) and the insoluble salts were filtered off through a pad of silica gel. The filtrate was concentrated under rotary evaporation at 40° C. to approximately 40 mL of volume to induce crystal formation. The mixture was cooled to ambient temperature and the crystals (8.13 g, 0.048 mol, 48% yield) were collected as a white powder. Furthermore, the process was conveniently carried out in a one-pot operation when the reaction was quenched with sodium bicarbonate and extracted with 1-butanol and ethyl acetate as described in Example 4.

Example 4

Preparation of Various azetidin-2-ones

The ketene acetal tris(trimethylsilyloxy)ethene is a commercially available product, and can be used for the synthesis of β-lactams starting from various aldehydes as depicted in Scheme 7 below. Thus, when benzaldehyde was treated with a THF solution of lithium hexamethyldisilazide at 0° C., the N-trimethylsilylbenzaldimine was generated instantaneously along with an equivalent of lithium trimethylsilanolate. Stirring this mixture with the ketene acetal at 10 to 15° C. for 14 h resulted in the formation of the β-lactams similar to the reaction in Scheme 7. This ketene acetal reaction was found to be general across various aromatic and enolizable aliphatics we examined (see Table I) and produced predominantly cis-β-lactams in all cases.

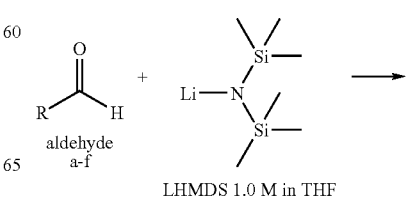

-continued

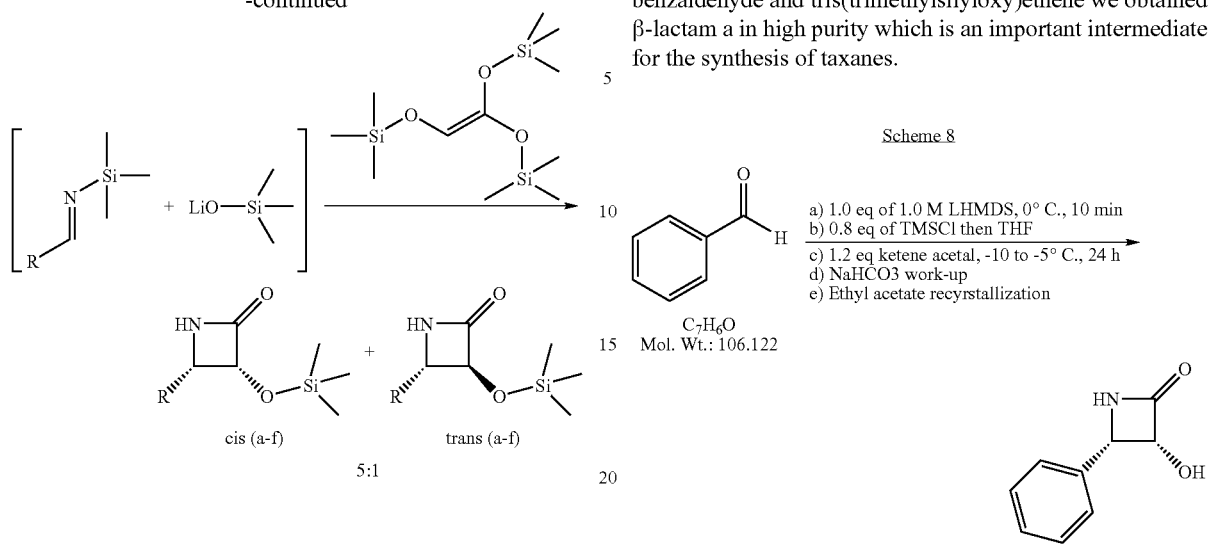

cis (a-f)   trans (a-f)

5:1

TABLE I

| | Aldehyde | Cis:trans |
|---|---|---|
| a | benzaldehyde | 5:1 |
| b | cyclopropanecarboxaldehyde | 3:1 |
| c | furan-2-carbaldehyde | 5:1 |
| d | thiophene-2-carbaldehyde | 5:1 |
| e | pyridine-2-carbaldehyde | 4:1 |
| f | cyclopentylacetaldehyde | 3:1 |

To optimize the reaction conditions, 0.8 equivalents of trimethylsilylchloride were added prior to the addition of the ketene acetal. This modification resulted in an increase in isolated yield to 66% of the product β-lactam a (Scheme 8).

Thus, in a single operation starting with the readily available benzaldehyde and tris(trimethylsilyloxy)ethene we obtained β-lactam a in high purity which is an important intermediate for the synthesis of taxanes.

Scheme 8

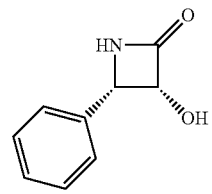

C$_7$H$_6$O
Mol. Wt.: 106.122 a) 1.0 eq of 1.0 M LHMDS, 0° C., 10 min
b) 0.8 eq of TMSCl then THF
c) 1.2 eq ketene acetal, -10 to -5° C., 24 h
d) NaHCO3 work-up
e) Ethyl acetate recyrstallization β-lactam a
C$_9$H$_9$NO$_2$
Mol. Wt.: 163.173
66% isolated yield In one experiment, a 0.5 M solution of LHMDS in THF was cooled to −10 to 0° C. then 1.0 equivalent of benzaldehyde was added over 15 min to control the exothermic imine reaction temperature to <15° C. Once the reaction temperature was −10 to −5° C., neat tris(trimethylsilyl)ethene (1.2 eq) was added. The mixture was stirred at this temperature over 14 h. Reaction completion was monitored by $^1$H NMR for the disappearance of the imine. Once complete, trimethylsilyl chloride (1 eq) was added to convert the lithium trimethylsilanoate to the volatile hexamethyldisiloxane. The reaction was washed twice with water at 1/10 the volume of reaction mixture to remove the lithium chloride salt. To the THF solution was added a catalytic amount of 1.0 M HCl and stirred for 2 h for complete desilylation the intermediate ($R_f$=0.8) as monitored by TLC analysis (EtOAc:Heptane, 3:1) to give the product ($R_f$=0.2). The hydrochloric acid in the reaction was quenched with triethylamine and the mixture was filtered through a pad of silica gel followed by exchange of the THF with ethyl acetate under rotary evaporation. The crystals were collected as a white solid and washed with cold ethyl acetate. β-lactam a: mp: 140 to 145° C.; $^1$H NMR (400 MHz, CDCl$_3$) (ppm): 2.26 (d, J=9.4 Hz, 1H), 4.96 (d, J=4.96 Hz, 1H, 5.12 (m, 1H), 4.15 (bm, 1H), 7.41 (m, 5H).

In another experiment, benzaldehyde was added to a 1.0 M THF solution of LHMDS (100 mL, 0.1 mol) at 0° C. and the mixture was stirred for 15 minutes followed by the addition of TMSCl (10 mL, 0.08 mol). To this solution was added tris (trimethylsilyloxy)ethylene (40 mL, 0.12 mol) and the mixture was stirred at −10 to −5° C. over 24 h. The mixture was warmed to ambient temperature over 2 h and quenched with saturated sodium bicarbonate (25 mL) and stirred at ambient temperature for 30 min and the layers were separated. The aqueous layer was back extracted with 1-butanol (200 mL) and the organic layers were combined and washed with brine (50 mL), dried over sodium sulfate, filtered through a pad of silica gel and concentrated to give a solid. The solid was taken up in hot ethyl acetate (800 mL) and the insoluble solids were filtered off through a pad of silica gel. The filtrate was concentrated under rotary evaporation at 40° C. to approximately 15 mL in volume to induce crystal formation. The mixture was cooled to ambient temperature and the crystals (10.73 g, 0.025 mol, 66% yield) were collected as a white powder. β-lactam a: mp: 140 to 145° C.; $^1$H NMR (400 MHz, CDCl$_3$) (ppm): 2.26 (d, J=9.4 Hz, 1H), 4.96 (d, J=4.96 Hz, 1H, 5.12 (m, 1H), 4.15 (bm, 1H), 7.41 (m, 5H).

Example 5

Trimethylsilyl 2-(trimethylsilyloxy)acetate

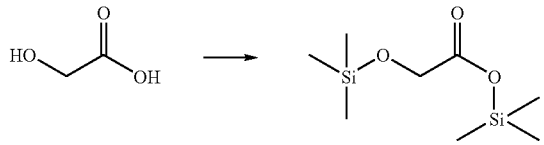

Glycolic acid (91.2 g, 2.4 mol) was dissolved in pyridine (194 g, 2.45 mol) and acetonitrile (600 mL) by mechanical stirring under nitrogen and reflux condensor. Trimethylsilylchloride (TMSCl, 260 g, 2.4 mol) was added via an addition funnel over 30 min. The mixture was stirred for 30 min and the hexanes (250 mL) was added and the phases were separated. To the bottom layer was added a second lot of hexanes (100 mL) and agitated vigorously for 5 minutes. Then the phases were separated and the hexanes layers were combined and concentrated under rotary evaporation at 30° C. to give 240 g (91%) of the known acetate.

Example 6

Tris(trimethylsiloxy)ethene

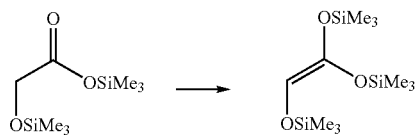

To a 0.5 M THF solution of LHMDS (200 mL, 0.1 mol) at 0° C. was added the trimethylsilyl-2-(trimethylsiloxy)acetate (23.9 mL, 0.1 mol) drop-wise over 15 minutes and the mixture was stirred at this temperature for an additional 15 min to generate the lithium enolate. Trimethylsilyl chloride (12.5 mL, 0.1 mol) was added over 15 minutes to trap the enolate as the tris(trimethylsiloxy)ethene product. The mixture was warmed to ambient temperature and the THF solvent was removed by vacuum rotary evaporation at 40° C. to precipitate out the lithium chloride. The mixture was taken up in 300 mL of hexanes and 5 mL of triethylamine and stirred for 5 min; the salt was allowed to settle. The supernatant was filtered through a pad of diatomaceous earth twice to give a clear solution. The solution was concentrated under rotary evaporation to give the lightly yellow colored oil product. The solution was concentrated under rotary evaporation to give the lightly yellow colored oil product identical to the commercial product. Bp=90° C. at 1 mmHg.

Example 7

N-trimethylsilyl-3-trimethylsiloxy-4-phenyl-azetidin-2-one

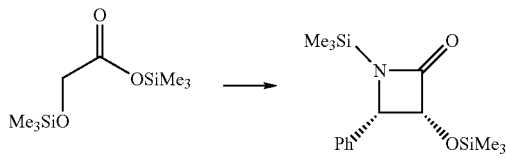

A one-pot procedure for the synthesis of previously unreported N-trimethylsilyl beta-lactam from the trimethylsilyl-2-trimethylsiloxy-acetate has been discovered to be an efficient economical method not requiring cryogenic cooling. To a magnetically stirring solution of hexamethyldisilazane (390 g, 2.42 mol) in dry 1,2-dimethoxyethane (505 mL) under nitrogen with a circulation chiller at 0° C. was added a 2.5 M solution of n-butyllithium (840 mL, 2.1 mol) at a rate so as to control the exothermic reaction temperature to <30° C. (over 45 min) to generate the required LHMDS base in situ. Once the LHMDS solution temperature has reached <10° C., a neat mixture of TMSCl (119.5 g, 1.1 mol) and the trimethylsilyl-2-(trimethylsiloxy)acetate (240 g, 1.1 mol) was added over 15 minutes to give the tris(trimethylsiloxy)ethene in situ. Then neat benzaldehyde (106.12 g, 1.0 mol) was added at a rate so as to control the exothermic reaction temperature to <25° C. to give the N-trimethylsilyl-benzaldimine in situ. The mixture was allowed to react at ambient temperature (22° C.) until $^1$H NMR monitoring indicated that the disappearance of the ketene acetal resonance at 5.4 ppm (CDCl$_3$) occurred at 12 h of reaction time. The reaction mixture was quenched with trimethylchlorosilane (TMSCl, 108.64 g, 1.0 mol), triethylamine (25.3 g, 0.25 mol) followed by acetic acid (6.0 g, 0.1 mol) while keeping the exothermic reaction temperature to <22° C. The mixture was diluted with hexanes (500 mL) and the resulting lithium chloride salt was filtered off through a pad of celite (200 g) followed by filter cake washing with hexanes (250 mL). The filtrate was concentrated under rotary vacuum evaporation to a residue. The residue was taken up in hexanes (500 mL) and allowed to stand at −25° C. to induce crystal formation. The white crystals were collected by vacuum filtration, washed with cold −20° C. hexanes (200 mL), and dried to a constant weight of 152 g. The filtrate was concentrated to a residue, taken up in hexanes (200 mL), and recrystallized as previous to give a second crop of 32 g. The crops were combined (184 g, 60% yield) and $^1$H NMR analysis found them to be pure cis-N-trimethylsilyl-3-trimethylsiloxy-4-phenyl-azetidin-2-one. Mp: 53 to 55° C. $^1$H NMR (400 MHz, CDCl$_3$) δ (ppm): 0.11 (s, 9H), 0.14 (s, 9H), 4.63 (d, J=5.01 Hz, 1H), 5.06 (d, J=5.01 Hz, 1H), 7.31 (m, 5H).

Example 8

Cis-3-Trimethylsiloxy-4-phenyl-azetidin-2-one

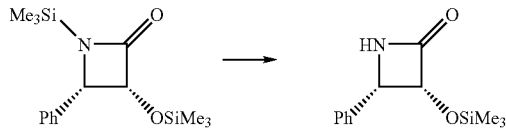

To a solution of N-trimethylsilyl-3-trimethylsiloxy-4-phenyl-azetidin-2-one (140 g, 0.46 mol) in hexanes (600 mL) at ambient temperature was added triethylamine (101 g, 1 mol), methanol (22 g, 0.7 mol) and the mixture was stirred for 15 minutes resulting in crystal formation of the N-desilylated product. The mixture was cooled to 0° C. for 15 min and the white crystals were collected by vacuum filtration, washed with cold hexanes, and dried to a constant weight of 94 g (87% yield). Mp: 118 to 120° C., $^1$H NMR (400 MHz, CDCl$_3$) δ (ppm): −0.08 (s, 9H), 4.79 (d, J=4.4 Hz, 1H), 5.09 (dd, J=4.4, 2.7 Hz, 1H), 6.16 (bm, 1H), 7.3 to 7.4 (m, 5H).

Example 9

Cis-3-hydroxy-4-phenyl-azetidin-2-one

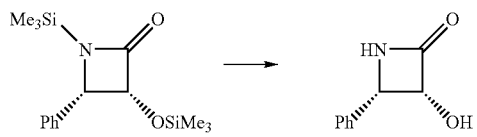

To a heterogeneous solution of N-trimethylsilyl-3-trimethylsiloxy-4-phenyl-azetidin-2-one (150 g, 0.49 mol) in methanol (500 mL) was added a catalytic amount of trimethylchlorosilane (1.08 g, 1 mmol) and the mixture was stirred at ambient temperature to give a clear solution. Thin layer chromatography (TLC) monitoring of the reaction eluting with ethyl acetate and hexanes (3:1) indicated that complete conversion was achieved after 15 minutes. The reaction mixture was quenched with triethylamine (10.1 g, 0.1 mol) and the methanol was removed under rotary evaporation at 40° C. until crystals formed. Ethyl acetate (300 mL) was added and the evaporation was continued to remove the remaining methanol to give a thick slurry before cooling to 0 to 5° C. for 20 minutes. The white crystals were collected via vacuum filtration following by washing with cold 0° C. ethyl acetate (75 mL) and dried to constant weight of 75 g (94% yield) of the desired product described previously.

Example 10

1-(triethylsilyloxy)-1,2-bis(trimethylsilyloxy)ethene

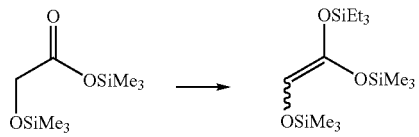

To a solution of diisopropylamine (15.5 mL, 0.11 mol) in THF (100 mL) at −78° C. was added a 1.6 M hexanes solution of n-butyl lithium (70 mL, 0.11 mol) over 15 minutes. After stirring for an additional 15 minutes at this temperature, triethylsilylchloride (16.7 mL, 0.1 mol) was added over 10 minutes followed by the addition of trimethylsilyl-2-(trimethylsiloxy)acetate (24.4 mL, 0.1 mol) over 30 minutes. The reaction was stirred at −78° C. for 30 minutes and warmed to ambient temperature by removing the cryogenic bath. The THF solvent was removed by vacuum rotary evaporation at 40° C. to precipitate out the lithium chloride. The mixture was taken up in 300 mL of hexanes and 5 mL of triethylamine and stirred for 5 min and the salt was allowed to settle. The supernatant was twice filtered through a pad of diatomaceous earth to give clear solution. The solution was concentrated under rotary evaporation to give the lightly yellow colored oil product as a mixture of geometrical isomers (4:1).

Example 11

Triethylsilyl-2-(triethylsilyloxy)acetate

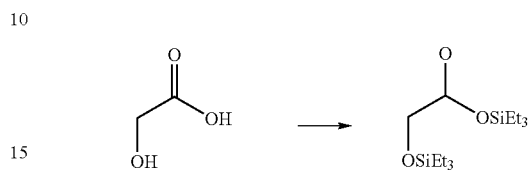

Glycolic acid (76.05 g, 1 mol) was dissolved in dry pyridine (164 mL, 2 mol) and the mixture was cooled to 0 to 5° C. with an ice-water bath with stirring. Neat triethylsilyl chloride (115 g, 1 mol) was added drop-wise to control the exotherm to less than 40° C. Pyridinium chloride precipitated as a free flowing solid. Heptane (500 mL) was added to aid the agitation. The second equivalent of neat triethylsilylchloride was added and the mixture was stirred as ambient temperature (22 to 40° C.) for 30 minutes until the reaction was complete. The mixture was further diluted with heptane (1 L) and the salt was allowed to precipitate out. The heptane layer was siphoned into the rotary evaporator through a medium porous inline filter and concentrated to give a clear oil (215 g, 0.98 mol) of the triethylsilyl-2-(triethylsilyloxy)acetate ester. The oil was further purified by vacuum distillation. Bp: 128 to 130° C., 1.5 mmHg. $^1$H NMR (400 MHz, CDCl$_3$) δ (ppm): 0.64 (q, J=8.04 Hz, 6H) 0.78 (q, J=8.04, 6H), 0.97 (t, J=8.04, 2x9H), 4.2 (s, 2H).

Example 12

Tris(triethylsiloxy)ethene

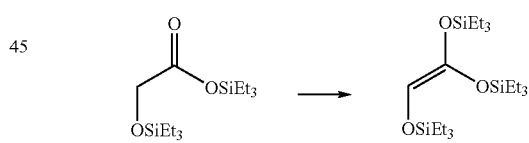

The ester was added to a 0.5 M THF (200 mL, 0.1 mol) solution over 15 minutes and the mixture was stirred at this temperature for an additional 15 minutes to generate the lithium enolate. Triethylsilyl chloride (16.7 mL 0.1 mol) was added over 15 minutes to trap the enolate as the tris(triethylsiloxy)ethene product. The mixture was warmed to ambient temperature and the THF solvent was removed by vacuum rotary evaporation at 40° C. to precipitate out the lithium chloride. The mixture was taken up in 300 mL of hexanes and 5 mL of triethylamine and stirred for 5 min while the salt was allowed to settle. The supernatant was twice filtered through a pad of diatomaceous earth to give a clear solution. The solution was concentrated under rotary evaporation to give the lightly yellow colored oil product.

In our experience, under standard conditions as used above in Example 4 for reaction of ketene acetals and imines to form β-lactams, tris(triethylsiloxy)ethene did not tend to react appreciably with an imine to form the desired β-lactam.

Example 13

1,2-bis(triethylsilyloxy)-1-(trimethylsilyloxy)ethene

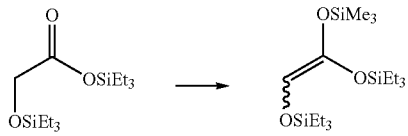

To a solution of diisopropylamine (15.5 mL, 0.11 mol) in THF (100 mL) at −78° C. was added a 1.6 M hexanes solution of n-butyl lithium (70 mL, 0.11 mol) over 15 minutes. After stirring for an additional 15 minutes at this temperature, triethylsilylchloride (16.7 mL, 0.1 mol) was added over 10 minutes followed by the addition of triethylsilyl 2-(triethylsiloxy)acetate (37.6 g, 0.1 mol) over 30 minutes. The reaction was stirred at −78° C. for 30 minutes and warmed to ambient temperature by removing the cryogenic bath and the THF solvent was removed by vacuum rotary evaporation at 40° C. to precipitate the lithium chloride. The mixture was taken up in 300 mL of hexanes and 5 mL of triethylamine and stirred for 5 minutes and the salt was allowed to settle. The supernatant was twice filtered through a pad of diatomaceous earth to give a clear solution. The solution was concentrated under rotary evaporation to give the lightly yellow colored oil product as a 1:1 mixture of geometrical isomers.

Example 14

Cis-3-triethylsiloxy-4-phenyl-azetidin-2-one

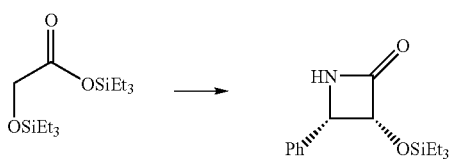

To a magnetically stirring solution of hexamethyldisilazane (39 g, 0.242 mol) in dry 1,2-dimethoxyethane (50 mL) under nitrogen with a circulation chiller at 0° C. was added a 2.5 M solution of n-butyllithium (84.0 mL, 0.21 mol) at a rate so as to control the exothermic reaction temperature to <30° C. (over 15 min) to generate the required LHMDS base in situ. Once the LHMDS solution temperature reached <−30° C., a neat solution of TMSCl (12 g, 0.11 mol) was added and the triethylsilyl-2-(triethylsiloxy)acetate (33.5 g, 0.11 mol) was added over 15 minutes to give the 1,2-bis(triethylsilyloxy)-1-(trimethylsilyloxy)ethene in situ as a mixture of geometrical isomers (6:1). Then, neat benzaldehyde (10.6 g, 0.10 mol) was added at a rate so as to control the exothermic reaction temperature to <−25° C. to give the N-trimethylsilyl-benzaldimine in situ. The hexanes solvent was removed under vacuum and the mixture was allowed to react at ambient temperature (22° C.) until $^1$H NMR monitoring indicated that the disappearance of the ketene acetal resonance at 5.43 ppm (CDCl$_3$) had occurred after 14 h of reaction time. The reaction mixture was quenched with trimethylchlorosilane (TMSCl, 10.8 g, 1.0 mol), triethylamine (2.53 g, 0.025 mol) and acetic acid (0.60 g, 0.01 mol) while keeping the exothermic reaction temperature to <22° C. The mixture was diluted with hexanes (50 mL) and resulting lithium chloride salt was filtered off through a pad of celite (20 g) followed by washing the filter cake with hexanes (25 mL). The filtrate was concentrated under rotary vacuum evaporation to a residue. The residue was taken up in hexanes (50 mL), triethylamine (5 mL) and methanol at ambient temperature and stirred for 15 minutes. TLC analysis of the mixture eluting with ethyl acetate:hexanes (2:1) indicated complete conversion to the desired product (R$_f$=0.45) after 10 minutes of reaction time. The mixture was then diluted with ethyl acetate (100 mL), filtered through a pad of silica gel (25 g) and concentrated until crystals formed. The crystals were collected via vacuum filtration, washed with hexanes and dried to a constant weight of 7.68 g as a white free flowing powder. Upon standing for 2 h at ambient temperature, the filtrate gave 2.8 g of a second crop after harvest. The combined yield was 38%. Mp: 98 to 100° C. $^1$H NMR (400 MHz, CDCl$_3$) δ (ppm): 0.44 (m, 6H), 0.78 (t, J=8.0 Hz, 9H), 4.80 (d, J=4.80, 1H), 5.08 (dd, 4.80, 2.80, 2H), 6.18 (bs, 1H), 7.28 to 7.38 (m, 5H).

Example 15

Cis-N-t-butoxycarbonyl-3-(2-methoxy-2-propoxy)-4-phenyl-azetidin-2-one

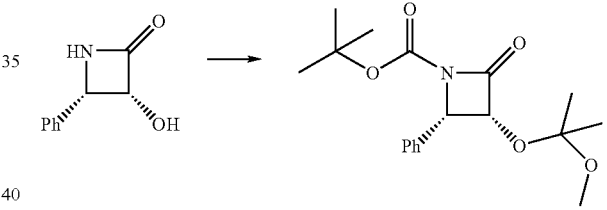

Racemic cis-3-hydroxy-4-phenyl-azetidin-2-one (100 g, 0.61 mol) was dissolved in THF (2.7 L) at ambient temperature at approximately 25 mL/g then cooled to −10 to −15° C. TsOH monohydrate catalyst (3.5 g, 0.018 mol, 3 mol %) was added and then 2-methoxy-propene (65 mL, 1.1 to 1.2 eq) was added drop-wise to control the exothermic reaction. The reaction was monitored by TLC and the 2-methoxypropene (2.9 mL) was charged as needed until the disappearance of the starting material was achieved. Triethylamine (85 mL, 0.612 mol) was added to quench the TsOH catalyst. Di-tert-butyl-dicarbonate (160.5 g, 0.735 mol, 1.2 eq) was added along with DMAP (2.25 g, 0.018 mol, 3 mol %) and the reaction was allowed to proceed at ambient temperature until complete. The mixture was diluted with heptane (1.97 L) approximately equal in volume to the THF used and filtered through a bed of silica gel (100 g) to remove the polar catalysts. The filter cake was washed with 1 L of a 1:1 mixture of ethyl acetate:heptane to ensure complete product recovery. The filtrate was concentrated until crystal formation occurred. Crystals were collected and washed with ice-cold heptane containing 2% triethylamine. The powder was dried to constant weight of 161.0 g (0.48 mol, 78%) under vacuum (0.1 mmHg) at ambient (22° C.) temperature. Mp: 90 to 92° C., $^1$H NMR (400 MHz, CDCl$_3$) δ (ppm): 0.92 (s, 3H), 1.21 (s, 3H), 1.37 (s, 9H), 1.58 (s, 3H), 3.12 (s, 3H), 5.03 (d, J=5.69 Hz, 1H), 5.17 (d, J=5.69 Hz, 1H), 7.33 (m, 5H).

Example 16

Racemic cis-3-trimethylsilyloxy-4-phenyl-azetidin-2-one

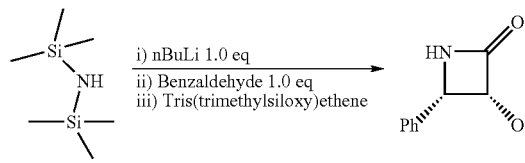

To a solution of hexamethyldisilazane (HMDS, 460 mL, 2.2 mol) in anhydrous dimethoxyethane (200 mL) at 0° C. was added a 2.5 M solution of n-butyllithium (nBuLi, 800 mL, 2.0 mol) over 45 min to maintain the reaction temperature at less than 40° C. After the addition, benzaldehyde was added to the reaction mixture over 1 h to maintain the reaction temperature at less than 40° C. After the addition was complete the mixture was cooled to 0° C. and tris(trimethylsiloxy) ethane (643 g, 2.2 mol) was added and the mixture was stirred until reaction was complete (12 h); reaction completion was determined by the disappearance of the starting ethene material. The reaction mixture was quenched with trimethylsilylchloride (TMSCl, 217.28 g, 1.0 eq), triethylamine (50 mL) and acetic acid (20 mL) and diluted with ethyl acetate (1.0 L). The lithium salt was filtered off via a sintered funnel. The filtrate was concentrated to dryness. The solid was taken up in heptane (1.0 L) and treated with methanol (96 g, 1.5 eq) at 20 to 40° C. to give crystals of the product. The solid product was collected via vacuum filtration through a Buchner funnel and washed with cold 15% ethyl acetate in heptane. The solid was taken up in ethyl acetate (1.5 L) and washed with brine, dried over sodium sulfate (200 g) and concentrated to give a white powder. Mp: 118 to 120°° C., $^1$H NMR (400 MHz, CDCl$_3$) δ (ppm): −0.08 (s, 9H), 4.79 (d, J=4.4 Hz, 1H), 5.09 (dd, J=4.4, 2.7 Hz, 1H), 6.16 (bm, 1H), 7.3 to 7.4 (m, 5H).

Example 17

Racemic cis-N-t-butoxycarbonyl-3-trimethylsilyloxy-4-phenyl-azetidin-2-one

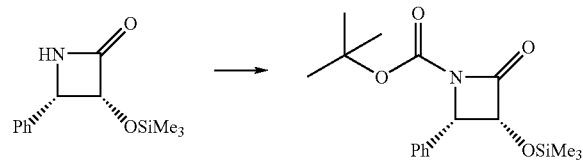

Racemic cis-3-trimethylsilyloxy-4-phenyl-azetidin-2-one (11.5 g, 48.9 mmol) was dissolved in tetrahydrofuran (THF, 250 mL) at ambient temperature under nitrogen and di-tert-butyldicarbonate was added along with N,N-4-dimethylaminopyridine (DMAP, 0.185 g, 1.5 mmol) and the mixture was magnetically stirred until the evolution of gas ceased. The mixture was filtered through a bed of silica gel (10 g) and concentrated on the rotary evaporator to give white solid product. The product was washed with cold heptane (50 mL) and collected by vacuum filtration and dried to a constant weight of 12.3 g (75%) at ambient temperature and vacuum (0.2 mmHg). Mp: 75 to 77° C., $^1$H NMR (400 MHz, CDCl$_3$) δ (ppm): −0.07 (s, 9H), 1.38 (s, 9H), 5.01 (d, J=5.6 Hz, 1H), 5.06 (d, J=5.6 Hz, 1H), 7.26 to 7.38 (m, 5H).

Example 18

Racemic (±)-Cis-N-t-butoxycarbonyl-3-diphenylmethylsilyloxy-4-phenyl-azetidin-2-one

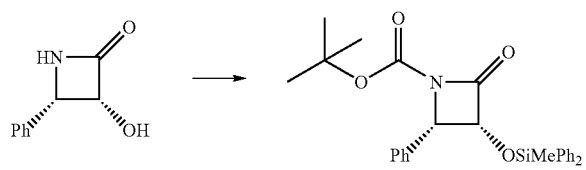

To a solution of racemic (±)-cis-3-hydroxy-4-phenyl-azetidin-2-one (4.5 g, 27.8 mmol) in THF (70 mL) under nitrogen was added triethylamine (8.4 g, 83.4 mmol), DMAP (100 mg, 0.83 mmol) and cooled to 0° C. Diphenylmethylsilyl chloride (7.1 g, 30.6 mmol) was added dropwise and the mixture was stirred at 0° C. for 30 min until complete disappearance of the starting material as shown by TLC eluting with 3:1 mixture of ethyl acetate and heptane. Di-tert-butyl-dicarbonate (Boc$_2$O, 6.68 g, 30.6 mmol) was added and the mixture was stirred at ambient temperature for 3 h for complete conversion to the desired product as shown by TLC (3:1 ethyl acetate:heptane). The mixture was diluted with heptane (150 mL) and filtered through silica gel (20 g) and the filtrate was concentrated to a solid. The solid was recrystallized from heptane (150 mL) to give a white powder (9.5 g, 74%). Mp 98° C., $^1$H NMR (400 MHz, CDCl$_3$) δ (ppm): 0.46 (s, 3H), 1.39 (s, 9H), 4.94 (d, J=5.5 Hz, 1H), 5.04 (d, J=5.5 Hz, 1H), 7.2 to 7.4 (m 15H).

What is claimed is:

1. A process for the preparation of cis-β-lactam (1A), the process comprising treating an imine (2) with a ketene acetal (3A) in the presence of a siloxide, $M^+O^-SiR_{51}R_{52}R_{53}$, to form a reaction product mixture comprising cis- and trans-β-lactams (1A) and (1B), with the ratio of cis-β-lactam (1A) to trans-β-lactam (1B) in the reaction product mixture being at least 3:1 (cis:trans), wherein the cis- and trans-β-lactams (1A) and (1B), the imine (2), and the ketene acetal (3A) correspond to Formulae (1A), (1B), (2), and (3A), respectively:

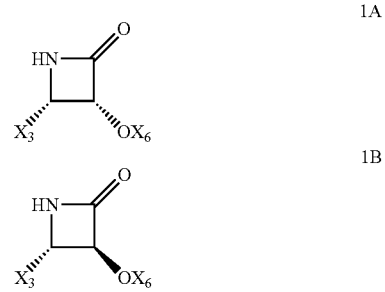

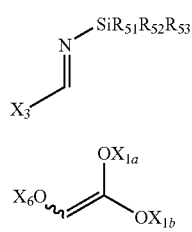

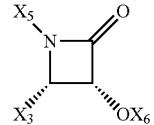

$M^+$ is a metal ion;

$X_{1a}$ and $X_{1b}$ are trimethylsilyl or $X_{1a}$ and $X_{1b}$ are triethylsilyl;

$X_3$ is phenyl, cyclopropyl, furyl, thienyl, pyridyl, or cyclopentyl;

$X_6$ is trimethylsilyl or triethylsilyl;

and —$SiR_{51}R_{52}R_{53}$ is trimethylsilyl or triethylsilyl.

2. The process of claim 1 wherein the imine (2) is prepared by treating an aldehyde having the formula $X_3C(O)H$ with a disilazide having the formula $MN(SiR_{51}R_{52}R_{53})_2$ wherein M is a metal.

3. The process of claim 1 wherein the siloxide is prepared by treating an aldehyde having the formula $X_3C(O)H$ with a disilazide having the formula $MN(SiR_{51}R_{52}R_{53})_2$ wherein M is a metal.

4. The process of claim 1 wherein the cis- and trans-β-lactams (1A) and (1B) are prepared in one vessel without isolation or purification of intermediates.

5. The process of claim 1 wherein a solvent for the reaction mixture comprises a polar aprotic solvent.

6. The process of claim 5 wherein the solvent comprises 1,2-dimethoxyethane.

7. The process of claim 1 further comprising converting the cis-β-lactam (1A) to a β-lactam having the structure of Formula (1AA)

wherein $X_3$ is phenyl, cyclopropyl, furyl, thienyl, pyridyl, or cyclopentyl;

$X_5$ is —$COX_{10}$, —$COOX_{10}$, trimethylsilyl, or triethylsilyl;

$X_6$ is trimethylsilyl or triethylsilyl; and $X_{10}$ is alkyl or aryl.

8. The process of claim 7 wherein $X_5$ is —$COX_{10}$, or —$COOX_{10}$.

9. The process of claim 8 wherein $X_{10}$ is phenyl, n-propyl, isopropyl, n-butyl, isobutyl, or tert-butyl.

10. The process of claim 8 wherein $X_5$ is —$COX_{10}$ wherein $X_{10}$ is phenyl, or —$COOX_{10}$ wherein $X_{10}$ is isopropyl, isobutyl, or t-butyl.

11. The process of claim 1 wherein $X_3$ is phenyl, furyl, or thienyl.

12. The process of claim 1 wherein $X_{1a}$, $X_{1b}$, and $X_6$ are trimethylsilyl.

13. The process of claim 1 wherein $X_{1a}$, $X_{1b}$, and $X_6$ are triethylsilyl.

14. The process of claim 1 wherein —$SiR_{51}R_{52}R_{53}$ is trimethylsilyl.

15. The process of claim 1 wherein $X_{1a}$, $X_{1b}$, $X_6$, and —$SiR_{51}R_{52}R_{53}$ are trimethylsilyl.

16. The process of claim 15 wherein $X_3$ is phenyl, furyl, or thienyl.

17. The process of claim 16 wherein the ratio of cis-β-lactam (1A) to trans-β-lactam (1B) in the reaction product mixture is at least 4:1 (cis:trans).

18. The process of claim 16 wherein the ratio of cis-β-lactam (1A) to trans-β-lactam (1B) in the reaction product mixture is at least 5:1 (cis:trans).

* * * * *